US011555089B2

(12) United States Patent
Tarao et al.

(10) Patent No.: US 11,555,089 B2
(45) Date of Patent: Jan. 17, 2023

(54) ROTAXANE AND POLYURETHANE USING THE SAME

(71) Applicants: SUMITOMO RUBBER INDUSTRIES, LTD., Kobe (JP); TOKYO INSTITUTE OF TECHNOLOGY, Tokyo (JP)

(72) Inventors: Toshiyuki Tarao, Kobe (JP); Mami Tanaka, Kobe (JP); Toshikazu Takata, Tokyo (JP); Jun Sawada, Tokyo (JP)

(73) Assignees: SUMITOMO RUBBER INDUSTRIES, LTD., Kobe (JP); TOKYO INSTITUTE OF TECHNOLOGY, Tokyo (JP)

(*) Notice: Subject to any disclaimer, the term of this patent is extended or adjusted under 35 U.S.C. 154(b) by 704 days.

(21) Appl. No.: 16/405,791

(22) Filed: May 7, 2019

(65) Prior Publication Data
US 2019/0367659 A1 Dec. 5, 2019

(30) Foreign Application Priority Data
May 30, 2018 (JP) .............................. JP2018-103437

(51) Int. Cl.
| | | |
|---|---|---|
| C08G 18/28 | (2006.01) | |
| C08G 18/12 | (2006.01) | |
| C08G 18/73 | (2006.01) | |
| C07D 323/00 | (2006.01) | |
| C08G 18/71 | (2006.01) | |
| C08G 18/38 | (2006.01) | |
| C08G 18/48 | (2006.01) | |
| C08G 18/66 | (2006.01) | |
| C08G 18/10 | (2006.01) | |

(52) U.S. Cl.
CPC ......... *C08G 18/285* (2013.01); *C07D 323/00* (2013.01); *C08G 18/10* (2013.01); *C08G 18/12* (2013.01); *C08G 18/283* (2013.01); *C08G 18/3831* (2013.01); *C08G 18/4854* (2013.01); *C08G 18/6685* (2013.01); *C08G 18/71* (2013.01); *C08G 18/73* (2013.01)

(58) Field of Classification Search
CPC .... C08G 18/285; C08G 18/12; C08G 18/283; C08G 18/73; C08G 18/10; C08G 18/3831; C08G 18/6685; C08G 18/71; C08G 18/4854; C07D 323/00
See application file for complete search history.

(56) References Cited

U.S. PATENT DOCUMENTS

| | | | | |
|---|---|---|---|---|
| 2013/0223886 A1* | 8/2013 | Miyagawa | ......... | G03G 15/0233 399/176 |
| 2019/0322815 A1* | 10/2019 | Sato | ....................... | B62D 29/04 |

FOREIGN PATENT DOCUMENTS

| | | |
|---|---|---|
| JP | 2012-224559 A | 11/2012 |
| JP | 2017-160164 A | 9/2017 |

OTHER PUBLICATIONS

Poster of Sawada et al., "Synthesis and Mechanical Property of Polyurethane Having Rotaxane Structure as Diol Component", The Society of Rubber Science and Technology, May 30, 2018, 1 page.
Poster of Sawada et al., "Synthesis and Mechanical Property of Rotaxane-based Polyurethane", Polymer Preprints, vol. 67, No. 1, May 8, 2018, 1 page.
Sawada et al., "Synthesis and Mechanical Property of Polyurethane Having Rotaxane Structure as Diol Component", The Society of Rubber Science and Technology, May 30, 2018, 1 page.
Sawada et al., "Synthesis and Mechanical Property of Rotaxane-based Polyurethane", Polymer Preprints, vol. 67, No. 1, May 8, 2018, 1 page.

* cited by examiner

*Primary Examiner* — Rabon A Sergent
(74) *Attorney, Agent, or Firm* — Birch, Stewart, Kolasch & Birch, LLP

(57) ABSTRACT

An object of the present invention is to provide a novel rotaxane and a polyurethane using the same. The present invention provides a rotaxane having a crown ether and a chain molecule piercing through the cyclic structure of the crown ether, wherein a hydroxyl group exists at one terminal of the chain molecule, and a hydroxyl group bonds to the cyclic structure of the crown ether. The present invention further provides a polyurethane using the rotaxane as a polyol component.

11 Claims, 6 Drawing Sheets

ROTAXANE AND POLYURETHANE USING THE SAME

FIELD OF THE INVENTION

The present invention relates to a novel rotaxane and a polyurethane using the same.

DESCRIPTION OF THE RELATED ART

A polymer having a rotaxane structure can disperse a stress due to the movability of the macromolecular chain at crosslinking points, and thus exhibits excellent toughness. Examples of the crosslinked polymer using the rotaxane include those disclosed in JP 2012-224559 A and JP 2017-160164 A.

JP 2012-224559 A discloses a rotaxane and a polymer using the same as a crosslinking agent, wherein the rotaxane comprises a wheel component composed of two crown ether molecules each having at least one polymerization active group; and an axis component piercing through a hole portion of the wheel component and represented by a general formula (I) $[R^1\text{-}R^2\text{—}N^+H_2\text{—}R^3\text{—}N^+H_2\text{—}R^2\text{-}R^4].2X^-$ (I) (In the formula, $R^1$ is a monovalent group having bulkiness equal to or larger than the hole of the crown ether, $R^2$ is a linear chain portion consisting of a divalent group and piercing through the hole of the crown ether, $R^3$ is a divalent group, $R^4$ is a monovalent group having bulkiness complementary to the hole of the crown ether, and $X^-$ is a monovalent anion).

JP 2017-160164 A discloses a rotaxane compound and a rotaxane network polymer using the same, wherein the rotaxane compound is composed of at least one cyclic molecule and one chain molecule piercing through the at least one cyclic molecule, where either one molecule of the at least one cyclic molecule and the one chain molecule has at least one reactive group selected from the group consisting of a nitrile oxide group and an azido group.

SUMMARY OF THE INVENTION

The object of the present invention is to provide a novel rotaxane and a polyurethane using the same.

The present invention provides a rotaxane having a crown ether and a chain molecule piercing through the cyclic structure of the crown ether, wherein the rotaxane has a structure with a hydroxyl group existing at one terminal of the chain molecule and a hydroxyl group bonding to the cyclic structure of the crown ether.

The present invention further provides a polyurethane comprising a polyisocyanate component and a rotaxane component as a constituent component, wherein the rotaxane component has a crown ether and a chain molecule piercing through the cyclic structure of the crown ether, wherein the rotaxane has a structure with a hydroxyl group existing at one terminal of the chain molecule and a hydroxyl group bonding to the cyclic structure of the crown ether.

The present invention also provides a polyurethane at least comprising a first urethane short chain and a second urethane short chain, wherein the first urethane short chain bonds to a cyclic structure of a crown ether at one terminal of the first urethane short chain, the second urethane short chain pierces through the cyclic structure of the crown ether of the first urethane short chain, and has blocking structures on both sides of the cyclic structure of the crown ether to prevent disassociation of the cyclic structure of the crown ether of the first urethane short chain from the second urethane short chain.

According to the present invention, a novel polyurethane different from the conventional polyurethane is provided.

DESCRIPTION OF THE PREFERRED EMBODIMENT

First, the rotaxane according to the present invention will be explained. The rotaxane according to the present invention has a crown ether and a chain molecule piercing through the cyclic structure of the crown ether, wherein the rotaxane has a structure with a hydroxyl group existing at one terminal of the chain molecule and a hydroxyl group bonding to the cyclic structure of the crown ether.

Figure 1:
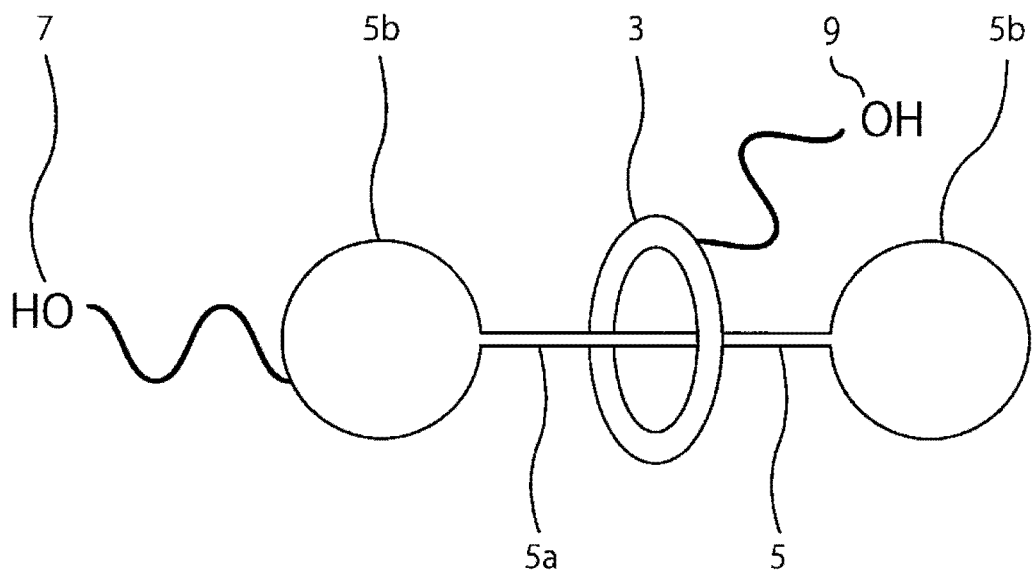
FIG. 1 is an illustrative figure schematically illustrating a structure of the rotaxane according to the present invention.

FIG. 1 is an illustrative figure schematically illustrating a structure of the rotaxane according to the present invention. A rotaxane 1 has a crown ether 3 and a chain molecule 5 piercing through the cyclic structure of the crown ether 3, wherein the rotaxane has a structure with a hydroxyl group 7 existing at one terminal of the chain molecule and a hydroxyl group 9 bonding to the cyclic structure of the crown ether 3. The chain molecule 5 has a chain portion 5a with a little steric hindrance piercing through the cyclic structure of the crown ether 3, and blocking structures 5b located on both terminal sides of the chain portion 5a with a little steric hindrance to prevent disassociation of the cyclic structure of the crown ether 3 from the chain molecule. The cyclic structure of the crown ether 3 is sandwiched between the two blocking structures 5b, and thus does not dissociate from the chain molecule 5. The rotaxane according to the present invention is characterized in that the cyclic structure of the crown ether 3 is rotatable around and movable along the chain portion 5a with a little steric hindrance of the chain molecule 5, and hydroxyl groups exist at the terminal of the chain molecule and on the cyclic structure of the crown ether, respectively.

The two existing hydroxyl groups enable the rotaxane according to the present invention to be used as, for example, a raw material for a polyurethane, polyester, and the like. In addition, since the cyclic structure of the crown ether is rotatable around and movable along the chain portion with a little steric hindrance of the chain molecule, the resultant polymer can disperse stress, thereby exerting excellent mechanical properties. The inner pore of the crown ether is preferably larger than the chain portion with a little steric hindrance of the chain molecule, and is preferably smaller than the blocking structure of the chain molecule.

The rotaxane according to the present invention comprises a crown ether having a hydroxyl group. The crown ether is a cyclic ether. Generally, the crown ether has a cyclic structure having an inner pore at the center, and the oxygen atom existing on the cyclic structure faces toward the inner pore. The oxygen atom of the cyclic structure of the crown ether electrostatically interacts with the cation, and the cation is taken into and kept in the inner pore. In other words, the crown ether is known as a so-called host-guest compound. The rotaxane according to the present invention preferably has one cyclic structure of the crown ether.

The atom constituting the cyclic structure of the crown ether preferably includes a carbon atom and an oxygen atom. The number of the atoms constituting the cyclic structure of the crown ether is preferably 12 or more, more preferably 15 or more, and is preferably 34 or less, more preferably 32 or less. In addition, among the number of the atoms constituting the cyclic structure, the number of the oxygen atoms is preferably 4 or more, more preferably 6 or more, and is preferably 12 or less, more preferably 10 or less. One to three atoms of the oxygen atoms constituting the cyclic structure may be optionally replaced with NH. NR, or S.

A benzene ring is preferably introduced in the cyclic structure of the crown ether. If the benzene ring is introduced, a functional group is easily introduced in the cyclic structure of the crown ether. The number of the introduced benzene ring is preferably, but not limited to, 1 to 4.

Specific examples of the crown ether include dibenzo-24-crown-8,24-crown-8, benzo-24-crown-8, and dicyclohexyl-24-crown-8. Among them, dibenzo-24-crown-8 and benzo-24-crown-8, each of which has a benzene ring in the cyclic structure, are preferable.

The hydroxyl group bonding to the cyclic structure of the crown ether may bond directly or indirectly to the cyclic structure. The "bonding indirectly" means bonding, e.g. via an alkylene chain having 1 to 10 carbon atoms. The hydroxyl group bonding to the cyclic structure more preferably bonds to the cyclic structure via an alkylene chain having 1 to 6 carbon atoms. In addition, the number of the hydroxyl group bonding to the cyclic structure of the crown ether preferably ranges from 1 to 5, more preferably 2 or less, and even more preferably 1.

The hydroxyl group bonding to the cyclic structure of the crown ether preferably bonds directly or indirectly to the benzene ring introduced in the cyclic structure of the crown ether. In a more preferable embodiment, the hydroxyl group preferably bonds to the benzene ring of the cyclic structure of the crown ether via an alkylene chain having 1 to 10 carbon atoms. In the case that a plurality of hydroxyl groups are introduced in the cyclic structure of the crown ether, a plurality of hydroxyl groups may be introduced in one benzene ring, or a plurality of benzene rings each having one hydroxyl group introduced may be disposed. The cyclic structure of the crown ether of the rotaxane according to the present invention preferably has two or less benzene rings each having one hydroxyl group introduced, more preferably has one benzene ring having one hydroxyl group introduced.

The rotaxane according to the present invention has a chain molecule piercing through the cyclic structure of the crown ether. The chain molecule preferably has a chain portion with a little steric hindrance and piercing through the cyclic structure of the crown ether, and blocking structures on both terminal sides of the chain portion with a little steric hindrance to prevent disassociation of the cyclic structure of the crown ether from the chain molecule. Examples of the chain portion with a little steric hindrance include an alkylene chain, a polyester chain, a polyether r chain, and a polyacrylic chain. Among them, the chain molecule preferably has an alkylene chain, more preferably has an alkylene chain having 3 to 30 carbon atoms, and even more preferably has an alkylene chain having 4 to 25 carbon atoms as the chain portion with a little steric hindrance.

The blocking structures for preventing disassociation of the cyclic structure of the crown ether from the chain molecule are formed on both terminal sides of the chain portion with a little steric hindrance of the chain molecule to sandwich the cyclic structure of the crown ether. The blocking structure is not particularly limited, as long as it has a more bulky structure than the inner pore of the crown ether, and examples thereof include alkylbenzene, dialkylbenzene, trityl, terphenyl, anthracene, bistrifluoromethylbenzene, fullerene and porphyrin.

The hydroxyl group existing at one terminal of the chain molecule may bond directly or indirectly to the blocking structure. The "bonding indirectly" means bonding to the blocking structure, e.g. via an alkylene chain having 1 to 10 carbon atoms.

The rotaxane according to the present invention is preferably a diol having two hydroxyl groups, or a triol having three hydroxyl groups.

Specifically, the rotaxane according to the present invention preferably has a structure represented by the following structural formula (1).

[Chemical formula 1]

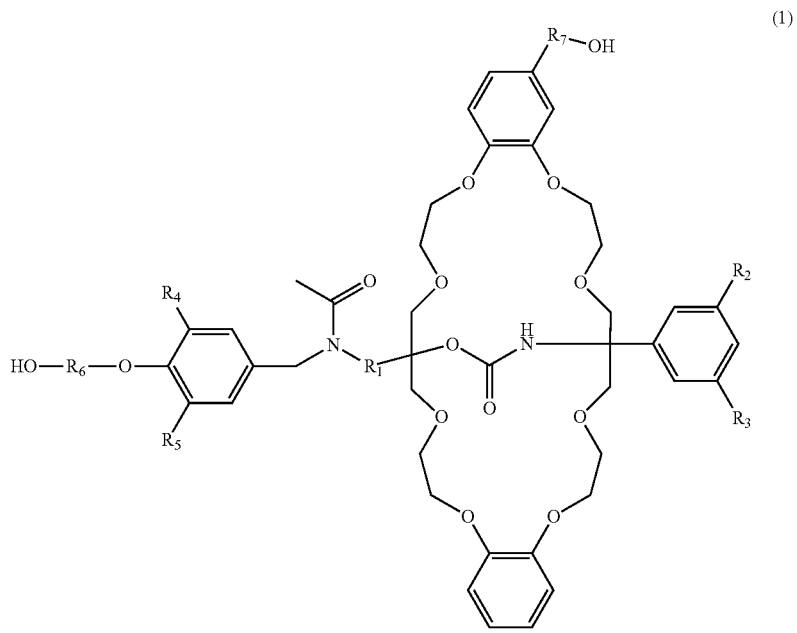

(1)

In the formula (1), $R_1$ represents an alkylene chain having 3 to 30 carbon atoms. $R_2$, $R_3$, $R_4$, $R_5$ may be identical to or different from each other, and represent an alkyl group having 1 to 10 carbon atoms. $R_6$ represents an alkylene chain having 1 to 10 carbon atoms. $R_7$ represents a single bond or an alkylene chain having 1 to 6 carbon atoms.

The crown ether structure in the structural formula (1) is dibenzo-24-crown-8, and has two benzene rings in the crown ether structure.

In the structural formula (1), the cyclic structure of the crown ether is preferably rotatable around and movable along the alkylene chain portion of $R_1$. From this viewpoint, $R_1$ is preferably a linear alkylene chain having 3 to 30 carbon atoms with a little steric hindrance. The alkylene chain represented by $R_1$ preferably has 4 or more carbon atoms, more preferably 6 or more carbon atoms, and even more preferably 8 or more carbon atoms, and preferably has 28 or less carbon atoms, more preferably 26 or less carbon atoms, and even more preferably 24 or less carbon atoms. If the number of carbon atoms falls within the above range, the resultant polyurethane has better mechanical properties.

Examples of $R_1$ include ethylene group, propylene group, butylene group, pentylene group, hexylene group, heptylene group, octylene group, nonylene group, decylene group, undecylene group, dodecylene group, tridecylene group, tetradecylene group, pentadecylene group, hexadecylene group, heptadecylene group, and octadecylene group. The alkylene group may be linear or branched, and is preferably linear.

$R_2$, $R_3$, $R_4$, $R_5$ may be identical to or different from each other, and represent an alkyl group having 1 to 10 carbon atoms. $R_2$, $R_3$, $R_4$, $R_5$ are preferably an alkyl group having 2 to 9 carbon atoms. Examples of the alkyl group having 1 to 10 carbon atoms include methyl group, ethyl group, propyl group, butyl group, pentyl group, hexyl group, heptyl group, octyl group, nonyl group, and decyl group. $R_2$, $R_3$, $R_4$, $R_5$ may be linear, branched or cyclic.

$R_6$ is preferably an alkylene group having 1 to 10 carbon atoms, more preferably an alkylene group having 2 to 9 carbon atoms. Examples of the alkylene group include ethylene group, propylene group, butylene group, pentylene group, hexylene group, heptylene group, octylene group, nonylene group, and decylene group. The alkylene group may be linear or branched, and is preferably linear.

$R_7$ is a single bond or an alkylene group having 1 to 10 carbon atoms. When $R_7$ is the single bond, it means that the hydroxyl group bonds directly to the benzene ring of the crown ether. $R_7$ is more preferably an alkylene group having 2 to 9 carbon atoms. Examples of the alkylene group include ethylene group, propylene group, butylene group, pentylene group, hexylene group, heptylene group, octylene group, nonylene group, and decylene group. The alkylene group may be linear or branched, and is preferably linear.

Specific examples of the rotaxane according to the present invention include a rotaxane with $R_1=C_{12}H_{24}$, $R_2=R_3=R_4=R_5=CH_3$, $R_6=C_2H_4$, and $R_7=CH_2$.

The method for producing the rotaxane according to the present invention comprises: a step (1) of providing a chain molecule, a step (2) of preparing a crown ether, and a step (3) of making the chain molecule pierce through the cyclic structure of the crown ether and simultaneously blocking a terminal of the chain molecule.

The step (1) of providing the chain molecule preferably comprises the following steps:

a step (1-1) of protecting a hydroxyl group of a blocking agent having the hydroxyl group, a step (1-2) of bonding the chain molecule to the blocking agent to produce a chain molecule having a blocking structure only at one terminal, a step (1-3) of introducing a hydroxyl group to another terminal of the chain molecule, and a step (1-4) of forming an ionic center in the chain molecule.

Specifically, the step (1-1) of protecting the hydroxyl group of the blocking agent having the hydroxyl group is preferably performed as follows.

(a) Dialkylhydroxy benzaldehyde is used as the blocking agent, and is reacted with a halogenated alcohol to obtain a reaction product 1 (dialkylhydroxyalkyloxo benzaldehyde). As the halogenated alcohol, for example, chloroethanol is suitably used. The reaction is preferably carried out, for example, at a temperature range of from 70° C. to 130° C. for 1 hour to 36 hours in N,N-dimethylformamide (DMF). In addition, in the reaction, a basic reagent for deprotonating dialkylhydroxy benzaldehyde is preferably used. Examples of the basic reagent include $K_2CO_3$.

(b) The obtained reaction product 1 is reacted with triisopropylsilyl chloride to obtain a reaction product 2 (dialkyltriisopropylsilyloxoalkyloxo benzaldehyde). By this reaction, the hydroxyl group of the blocking agent is protected. The reaction is preferably carried out, for example, at a temperature range of from 20° C. to 50° C. for 5 hours to 15 hours in N,N-dimethylformamide (DMF). The reaction is preferably carried out in the presence of a nucleophilic catalyst. Examples of the nucleophilic catalyst include imidazole.

(c) The reaction product 2 is reacted with an aminoalkylcarboxylic acid ester to obtain a reaction product 3 having —C═N— bond. The aminoalkylcarboxylic acid ester may be used as a hydrochloride. The reaction is preferably carried out, for example, at a temperature range of from 90° C. to 110° C. for 12 hours to 48 hours in toluene. An aminoalkylalcohol may be used instead of the aminoalkylcarboxylic acid ester. In this case, the following step (e) can be omitted.

(d) The —C═N— bond of the reaction product 3 is reduced to obtain a reaction product 4 having —CH—NH— bond. As the reducing agent, for example, $NaBH_4$, $NaBH_3CN$, $NaBH(OAc)_3$, or the like are preferably used. The reaction is preferably carried out, for example, at a temperature range of from 0° C. to 30° C. for 2 hours to 16 hours in methanol.

(e) The ester bond of the reaction product 4 is reduced to obtain a reaction product 5 having a hydroxyl group at the terminal of the alkyl chain. By this reaction, the ester moiety of the carboxylic acid is methylolated. As the reducing agent, for example, $LiAlH_4$. $LiBH_4$, or the like are preferably used. The reaction is preferably carried out, for example, at a temperature range of from 10° C. to 40° C. for 8 hours to 16 hours in tetrahydrofuran.

(1-4) The reaction product 5 is ionized with an ammonium salt to obtain a reaction product 6 (chain molecule) having an ionic center formed. The ammonium salt is not particularly limited, and examples thereof include ammonium hexafluorophosphate, ammonium trifluoromethanesulfonate, and ammonium trifluoroacetate, and ammonium hexafluorophosphate is preferable. Specifically, nitrogen of the —CH—NH— bond produced in (d) is cationized. The reaction product 6 is a chain molecule having a blocking structure only at one terminal, having an ionic center, and having a hydroxyl group at another terminal (the side opposite to the blocking structure). The ionic center is preferably formed on the blocking structure side of the chain molecule.

The step (2) of preparing the crown ether preferably comprises the following steps.

Step (2-1) of Protecting the Hydroxyl Group of the Crown Ether Having the Hydroxyl Group (a) Monoformyl crown ether is reduced to form a hydroxyl group, and the hydroxyl group is reacted with triisopropylsilyl chloride to obtain a reaction product 7 having a cyclic structure of the crown ether whose hydroxyl group has been protected. As the reducing agent, for example, $NaBH_4$, $NaBH_3CN$, $NaBH(OAc)_3$, or the like are preferably used. The reduction reaction is preferably carried out, for example, at a temperature range of from 0° C. to 30° C. for 2 hours to 6 hours in methanol. By this reduction reaction, the aldehyde is reduced to generate a methylol group (a hydroxyl group bonding to, via a methylene group,) on the benzene ring of the crown ether. In addition, the reaction between the hydroxyl group and the triisopropylsilyl chloride is preferably carried out, for example, at a temperature range of from 20° C. to 50° C. for 5 hours to 20 hours in DMF. By this reaction, the hydroxyl group of the crown ether is protected. In addition, the protection reaction of the hydroxyl group is preferably carried out in the presence of a nucleophilic catalyst. Examples of the nucleophilic catalyst include imidazole.

The step (3) of making the chain molecule pierce through the cyclic structure of the crown ether and simultaneously blocking the terminal of the chain molecule preferably comprises the following steps:

a step (3-1) of making the terminal where the hydroxyl group exists, of the chain molecule having the blocking structure only at one terminal and having the ionic center, pierce through the cyclic structure of the crown ether, and electrostatically bonding the cyclic structure of the crown ether and the ionic center of the chain molecule, a step (3-2) of allowing the hydroxyl group of the chain molecule to react with a blocking agent, a step (3-3) of eliminating the electrostatic bonding between the ionic center of the chain molecule and the cyclic structure of the crown ether structure, and a step (3-4) of removing the protection agent to generate the hydroxyl group.

Step (3-1) of making the terminal where the hydroxyl group exists, of the chain molecule having the blocking structure only at one terminal and having the ionic center, pierce through the cyclic structure of the crown ether, and electrostatically bonding the cyclic structure of the crown ether and the ionic center of the chain molecule (1) The hydroxyl group terminal of the reaction product 6 that is the chain molecule is made pierce through the cyclic structure of the crown ether of the reaction product 7, and simultaneously the ionic center of the reaction product 6 and the cyclic structure of the crown ether are electrostatically bonded. In other words, when the reaction product 6 that is the chain molecule is being in a state of piercing through the cyclic structure of the crown ether, the cationized nitrogen atom in the reaction product 6 is electrostatically kept by the opening of the cyclic structure of the crown ether. The cation of the chain molecule exists at a location near the blocking structure blocking one terminal of the chain molecule. Thus, the cyclic structure of the crown ether electrostatically bonds to the chain molecule at the location near the blocking structure blocking one terminal of the chain molecule. Specifically, dehydrated dichloromethane is added in a mixture of the reaction product 6 and the reaction product 7, and ultrasonic radiation is conducted to form the complex.

Step (3-2) of Allowing the Hydroxyl Group Terminal of the Chain Molecule to React with the Blocking Agent (a) The hydroxyl group existing at another terminal of the reaction product 6 that is the chain molecule is reacted with the blocking agent to obtain a reaction product 8. As the blocking agent, for example, a bulky polyisocyanate is preferably used. For example, dialkylphenyl isocyanate is preferably used. Examples of the dialkylphenyl isocyanate include 3,5-dimethylphenyl isocyanate, 3,5-di-tert-butylphenyl isocyanate, mesitylene isocyanate, 3,5-dimethoxyphenyl isocyanate, and 3,5-bistrifluoromethylphenyl isocyanate. The blocking reaction can be carried out, for example, at a temperature range of from 10° C. to 30° C. for 2 hours to 6 hours in dichloromethane. In addition, the reaction is preferably carried out in the presence of a conventional catalyst (excluding a basic catalyst) used in a reaction between an isocyanate group and a hydroxyl group. The reaction is preferably carried out, for example, in the presence of dibutyltin dilaurate. By this reaction, the cyclic structure of the crown ether is sandwiched between and hence blocked by the two blocking structures of the chain molecule.

Step (3-3) of Eliminating the Electrostatic Bonding Between the Chain Molecule and the Cyclic Structure of the Crown Ether The cationized nitrogen of the chain molecule is preferably neutralized, and acetylated by a reaction with acetic acid anhydride. As the neutralizing agent, triethylamine, diisopropylethylamine, and DBU (1,8-diazabicyclo[5.4.0]undec-7-ene) can be used. The reaction is preferably carried out, for example, at a temperature range of from 40° C. to 60° C. for 12 hours to 36 hours in tetrahydrofuran (THF). By this reaction, the ionic center of the reaction product 6 disappears, thus the electrostatic bonding between the chain molecule and the cyclic structure of the crown ether is eliminated.

Step (3-4) of Removing the Protection Agent to Generate the Hydroxyl Group

The triisopropylsilyl group protecting the hydroxyl group is eliminated to regenerate the hydroxyl group. By this elimination reaction, a hydroxyl group is generated at one terminal of the chain molecule, and a hydroxyl group bonding to the cyclic structure of the crown ether is generated. The reaction is preferably carried out, for example, at a temperature range of from 20° C. to 50° C. for 4 hours to 10 hours in tetrahydrofuran (THF). In this elimination reaction, for example, tetra n-butyl ammonium fluoride (TBAF) is preferably used. TBAF provides a fluoride ion source necessary for the deprotection of silylether.

The polyurethane according to the present invention comprises a polyisocyanate component and the rotaxane component of the present invention as a constituent component, wherein the rotaxane component has a crown ether and a chain molecule piercing through the cyclic structure of the crown ether, wherein the rotaxane has a structure with a hydroxyl group existing at one terminal of the chain molecule and a hydroxyl group bonding to the cyclic structure of the crown ether.

The polyurethane according to the present invention comprises (A) a polyisocyanate component and (B) a rotaxane component as a constituent component. The polyurethane is a polyurethane having a plurality of urethane bonds, obtained by a reaction between (A) the polyisocyanate component and (B) the rotaxane component.

(A) The polyisocyanate component is not particularly limited, as long as it has two or more isocyanate groups, and examples thereof include an aromatic polyisocyanate, an alicyclic polyisocyanate, and an aliphatic polyisocyanate. Examples of the aromatic polyisocyanate include 2,4-toluene diisocyanate, 2,6-toluene diisocyanate, a mixture of 2,4-toluene diisocyanate and 2,6-toluene diisocyanate (TDI), 4,4'-diphenylmethane diisocyanate (MDI), 1,5-naphthylene diisocyanate (NDI), 3,3'-bitolylene-4,4'-diisocyanate (TODI), xylylene diisocyanate (XDI), tetramethylxylylenediisocyanate (TMXDI), and para-phenylene diisocyanate (PPDI). Examples of the alicyclic polyisocyanate or aliphatic polyisocyanate include 4,4'-dicyclohexylmethane diisocyanate ($H_{12}$MDI), hydrogenated xylylenediisocyanate ($H_6$XDI), hexamethylene diisocyanate (HDI), isophorone diisocyanate (IPDI), and norbomene diisocyanate (NBDI). The polyisocyanate may be used solely or as a mixture of at least two of them.

In view of improving the abrasion resistance, the aromatic polyisocyanate is preferably used as (A) the polyisocyanate component. Use of the aromatic polyisocyanate enhances the mechanical property of the obtained polyurethane and provides a cover having an excellent abrasion resistance. In addition, in view of improving the weather resistance, as (A) the polyisocyanate component, a non-yellowing type polyisocyanate (e.g. TMXDI, XDI, HDI, $H_6$XDI, IPDI, $H_{12}$MDI and NBDI) is preferably used, 4,4'-dicyclohexylmethane diisocyanate ($H_{12}$MDI) is more preferably used. Since 4,4'-dicyclohexylmethane diisocyanate ($H_{12}$MDI) has a rigid structure, the mechanical property of the resulting polyurethane is enhanced, and thus a polyurethane having an excellent abrasion resistance is obtained.

The polyurethane according to the present invention may further contain (C) a polyol component. (C) The polyol component is not particularly limited, as long as it differs from (B) the rotaxane component and has a plurality of hydroxyl groups, and examples thereof include a low molecular weight polyol and a high molecular weight polyol.

Examples of the low molecular weight polyol include a diol such as ethylene glycol, diethylene glycol, triethylene glycol, propanediol (e.g. 1,2-propanediol, 1,3-propanediol, 2-methyl-1,3-propanediol, and the like), dipropylene glycol, butanediol (e.g. 1,2-butanediol, 1,3-butanediol, 1,4-butanediol, 2,3-butanediol, 2,3-dimethyl-2,3-butanediol, and the like), neopentyl glycol, pentanediol, hexanediol, heptanediol, octanediol, 1,4-cyclohexanedimethylol, aniline diol, and bisphenol A type diol; a triol such as glycerin, trimethylolpropane, and hexanetriol; and a tetraol or a hexol such as pentaerythritol and sorbitol.

Examples of the high molecular weight polyol include a polyether polyol such as polyoxyethylene glycol (PEG), polyoxypropylene glycol (PPG), and polyoxytetramethylene glycol (PTMG); a condensed polyester polyol such as polyethylene adipate (PEA), polybutylene adipate (PBA), and polyhexamethylene adipate (PHMA); a lactone polyester polyol such as poly-ε-caprolactone (PCL); a polycarbonate polyol such as polyhexamethylene carbonate; and an acrylic polyol.

The number average molecular weight of the high molecular weight polyol, for example, is preferably 400 or more, more preferably 1,000 or more, without particular limitation. If the number average molecular weight of the high molecular weight polyol is excessively low, the obtained polyurethane is hard. The upper limit of the number average molecular weight of the high molecular weight polyol is preferably 10,000, more preferably 8,000, without particular limitation. It is noted that the number average molecular weight is measured by gel permeation chromatography (GPC), using polystyrene as a standard material, N,N-dimethyl formamide (DMF) in which 5 mM of LiBr is added (30° C., flow: 0.7 mL) as an eluate, and two of TSK-GEL SUPERH2500 (available from Tosoh Corporation) as a column.

The constituent ratio of (A) the polyisocyanate component, (B) the rotaxane component and (C) the polyol component constituting the polyurethane is as follows. A molar ratio (NCO/OH) of the isocyanate group (NCO) of the polyisocyanate component to the total hydroxyl group (OH) of (B) the rotaxane component and (C) the polyol component is preferably 0.9 or more, more preferably 0.95 or more, and even more preferably 1.0, and is preferably 1.2 or less, more preferably 1.1 or less, and even more preferably 1.05 or less. If NCO/OH falls within the above range, a polyurethane having a high molecular weight is obtained.

A molar ratio (B/C) of (B) the rotaxane component to (C) the polyol component is preferably 0.01 or more, more preferably 0.03 or more, and even more preferably 0.05 or more, and is preferably 1.0 or less, more preferably 0.9 or less, and even more preferably 0.8 or less.

The polyurethane according to the present invention may further contain (D) a polyamine as a constituent component, in addition to (A) the polyisocyanate component, (B) the rotaxane component and (C) the polyol component. The polyamine is not particularly limited, as long as it has at least two amino groups. Examples of the polyamine include an aliphatic polyamine, an alicyclic polyamine, and an aromatic polyamine. Examples of the aliphatic polyamine include ethylenediamine, propylenediamine, butylenediamine, and hexamethylenediamine. Examples of the alicyclic polyamine include isophoronediamine and piperazine.

The constitutional embodiment of the polyurethane according to the present invention is not particularly limited, and examples thereof include an embodiment where the polyurethane is formed from (A) the polyisocyanate component and (B) the rotaxane component; an embodiment where the polyurethane is formed from (A) the polyisocyanate component, (B) the rotaxane component and (C) the polyol component; and an embodiment where the polyurethane is formed from (A) the polyisocyanate component. (B) the rotaxane component, (C) the polyol component and (D) the polyamine component.

The polyurethane according to the present invention may be either a thermoplastic polyurethane or a thermosetting polyurethane. The thermoplastic polyurethane is a polyurethane exhibiting plasticity by heating and generally means a polyurethane having a linear chain structure of a high-molecular weight to a certain extent. The thermosetting polyurethane is a polyurethane obtained through a curing reaction between a relatively low molecular weight prepolymer and a curing agent when using. By controlling the number of the functional group of the prepolymer or the curing agent to be used, a thermosetting polyurethane having a three-dimensional crosslinked structure is formed. As the polyurethane according to the present invention, a thermoplastic polyurethane is preferred.

Examples of the method for synthesizing the polyurethane according to the present invention include a one-shot method and a prepolymer method. The one-shot method is a method of reacting a polyisocyanate component and a polyol component or the like at one time. The prepolymer method is a method of reacting a polyisocyanate component and a polyol component or the like in multiple steps, e.g. a method of synthesizing a urethane prepolymer having a relatively low molecular weight, followed by further polymerization to have a higher molecular weight.

Next, the method for synthesizing the polyurethane according to the present invention by the prepolymer method will be described. In the prepolymer method, for example, (A) the polyisocyanate component, (B) the rotaxane component and (C) the high molecular weight polyol component are reacted to synthesize a prepolymer, and subsequently the obtained prepolymer is reacted with a low molecular weight polyol to perform a chain extension reaction. It is noted that (B) the rotaxane component may be used as a chain extender. In the following, in the description regarding the synthesis conditions of the polyurethane, the synthesis of the prepolymer and the chain extension reaction are collectively simply referred to as "synthesis of polyurethane", unless specified otherwise.

The temperature at which the synthesis reaction of the polyurethane is carried out is preferably 10° C. or more, more preferably 30° C. or more, and even more preferably 50° C. or more, and is preferably 200° C. or less, more preferably 150° C. or less, and even more preferably 100° C. or less. In addition, the reaction time is preferably 10 minutes or more, more preferably 1 hour or more, and even more preferably 3 hours or more, and is preferably 32 hours or less, more preferably 16 hours or less, and even more preferably 8 hours or less.

The synthesis reaction of the polyurethane is preferably conducted in an atmosphere of dry nitrogen.

In synthesizing the polyurethane, a conventional catalyst may be used. Examples of the catalyst include a monoamine such as triethylamine and N,N-dimethylcyclohexylamine; a polyamine such as N,N,N',N'-tetramethylethylene diamine and N,N,N',N'',N''-pentamethyldiethylene triamine; a cyclic diamine such as 1,8-diazabicyclo-[5.4.0]-7-undecene (DBU) and triethylenediamine; and a tin-based catalyst such as dibutyl tin dilaurylate and dibutyl tin diacetate. These catalysts may be used solely, or two or more of these catalysts may be used in combination. Among them, the tin-based catalyst such as dibutyl tin dilaurylate and dibutyl tin diacetate is preferable, and in particular, dibutyl tin dilaurylate is suitably used.

The present invention includes a polyurethane at least comprising a first urethane short chain and a second urethane short chain, wherein the first urethane short chain bonds to a cyclic structure of a crown ether at one terminal of the first urethane short chain, the second urethane short chain pierces through the cyclic structure of the crown ether of the first urethane short chain, and has blocking structures on both sides of the cyclic structure of the crown ether to prevent disassociation of the cyclic structure of the crown ether of the first urethane short chain from the second urethane short chain.

Figure 2:
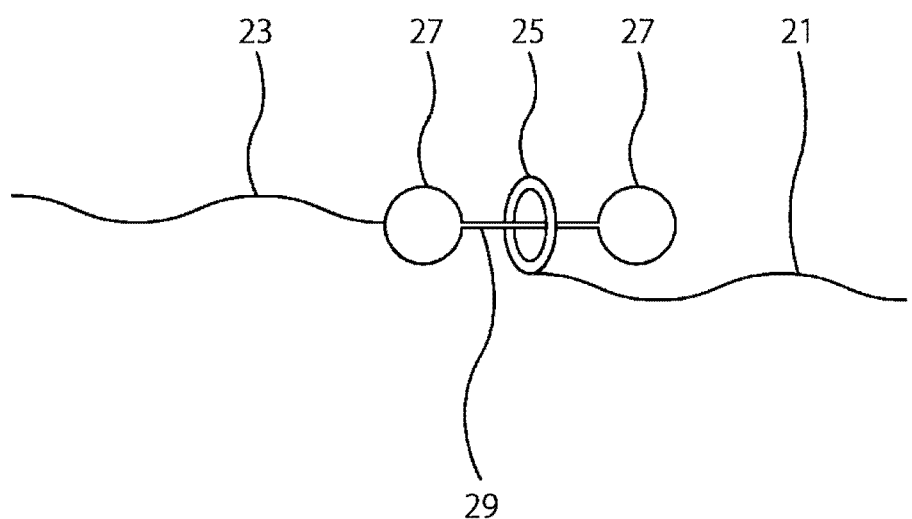
FIG. 2 is an illustrative figure schematically illustrating a structure of the polyurethane according to the present invention.

FIG. 2 is an illustrative figure schematically illustrating the polyurethane. A polyurethane 20 comprises a first urethane short chain 21 and a second urethane short chain 23. The first urethane short chain 21 bonds to a cyclic structure 25 of a crown ether at one terminal of the first urethane short chain 21. The second urethane short chain 23 pierces through the cyclic structure 25 of the crown ether of the first urethane short chain 21. The second urethane short chain 23 comprises a chain portion 29 with a little steric hindrance and piercing through the cyclic structure 25 of the crown ether, and blocking structures 27 on both terminal sides of the chain portion 29 with a little steric hindrance to prevent disassociation of the cyclic structure 25 of the crown ether from the second urethane short chain 23. The cyclic structure 25 of the crown ether of the first urethane short chain 21 is blocked by being sandwiched between the two blocking structures 27 with a large steric hindrance, which prevents the cyclic structure 25 of the crown ether from disassociating from the second urethane short chain 23. In other words, the first urethane short chain 21 and the second urethane short chain 23 are connected by a steric hindrance other than a covalent bond. The cyclic structure 25 of the crown ether is rotatable around and movable along the chain portion 29 with a little steric hindrance, thus when a load is applied to the resulting polyurethane, the stress can be dispersed.

Herein, a chain molecule serving as an element constituting a final polyurethane is referred to as a urethane short chain. The urethane short chain is preferably, for example, a urethane prepolymer obtained by a reaction between a polyisocyanate and a polyol.

Figure 3:
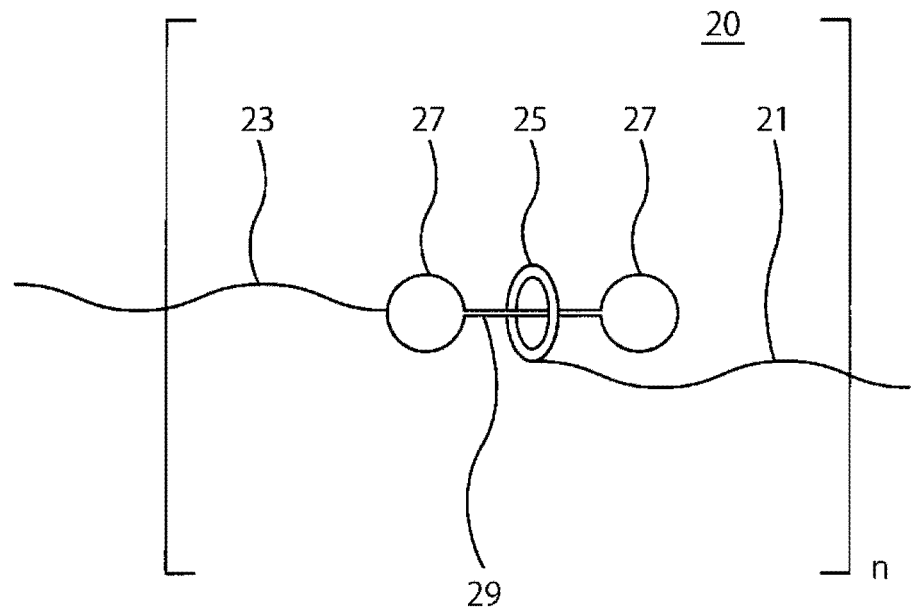
FIG. 3 is an illustrative figure schematically illustrating a structure of the polyurethane according to the present invention.

The polyurethane according to the present invention is preferably a polyurethane where the above exemplified urethane short chain 21 is connected repeatedly via a steric hindrance between the cyclic structure and the blocking structure other than via a covalent bond. FIG. 3 shows a repeating unit constituting the polyurethane according to the present invention, n is an integer of 1 or more, n is preferably 50 or more, more preferably 100 or more.

Figure 4:
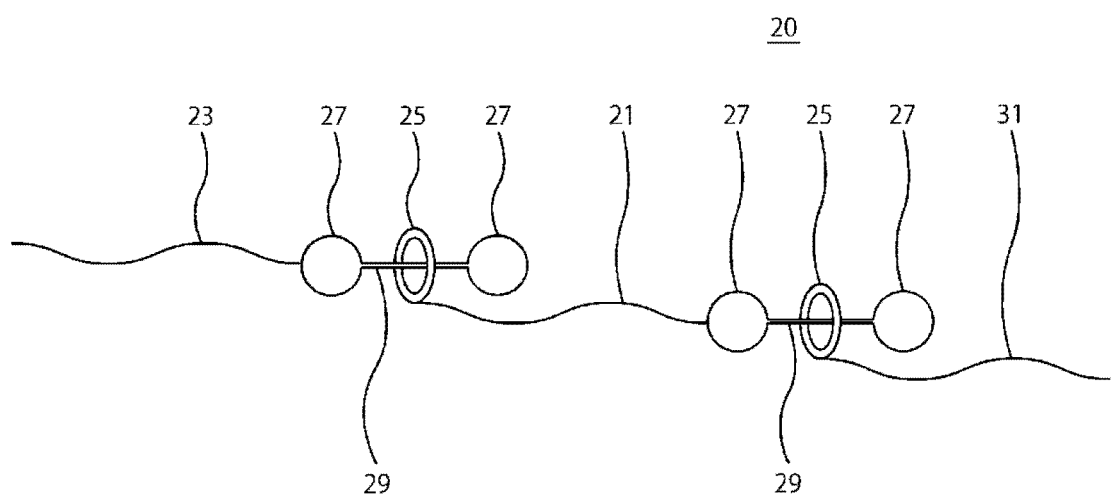
FIG. 4 is an illustrative figure schematically illustrating a structure of the polyurethane according to the present invention.

FIG. 4 is an illustrative figure schematically illustrating the polyurethane according to the present invention further comprising a third urethane short chain 31 in addition to the first and second urethane short chains. The third urethane short chain 31 bonds to a cyclic structure 25 of a crown ether at one terminal of the third urethane short chain 31. The first urethane short chain 21 pierces through the cyclic structure 25 of the crown ether of the third urethane short chain 31, and blocking structures 27 are formed on the first urethane short chain 21 and on both sides of the cyclic structure 25 of the crown ether to prevent disassociation of the cyclic structure 25 of the crown ether of the third urethane short chain 31 from the first urethane short chain 21.

In this case, the urethane short chain 21 has a cyclic structure 25 of a crown ether at one terminal and two sterically bulky blocking structures 27 at another terminal. A chain portion 29 with a little steric hindrance exists between the two blocking structures 27.

It is noted that, as shown in FIG. 4, for example, a urethane chain 23 located at one terminal of the polyurethane may not have a cyclic structure of a crown ether. Similarly, a urethane chain 31 constituting another terminal of the polyurethane may not have a blocking structure for blocking a cyclic structure 25 of a crown ether.

Figure 5:
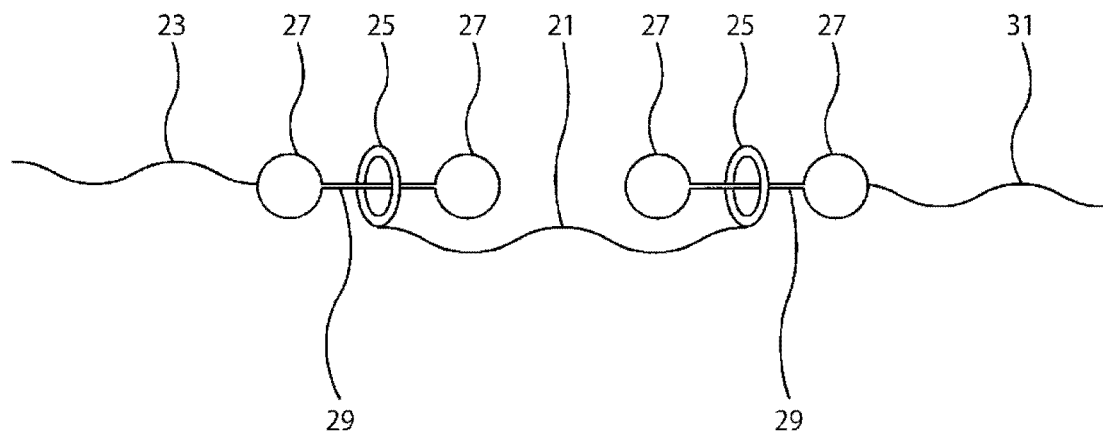
FIG. 5 is an illustrative figure schematically illustrating a structure of the polyurethane according to the present invention.

FIG. 5 is an illustrative figure schematically illustrating another embodiment of the polyurethane according to the present invention further comprising a third urethane short chain 31 in addition to the first and second urethane short chains. Both terminals of the first urethane short chain 21 bond to a cyclic structure 25 of a crown ether. In other words, the first urethane short chain 21 crosslinks the cyclic structure 25 of the crown ether blocked by the second urethane short chain 23 and the cyclic structure 25 of the crown ether blocked by the third urethane short chain 31.

Figure 6:
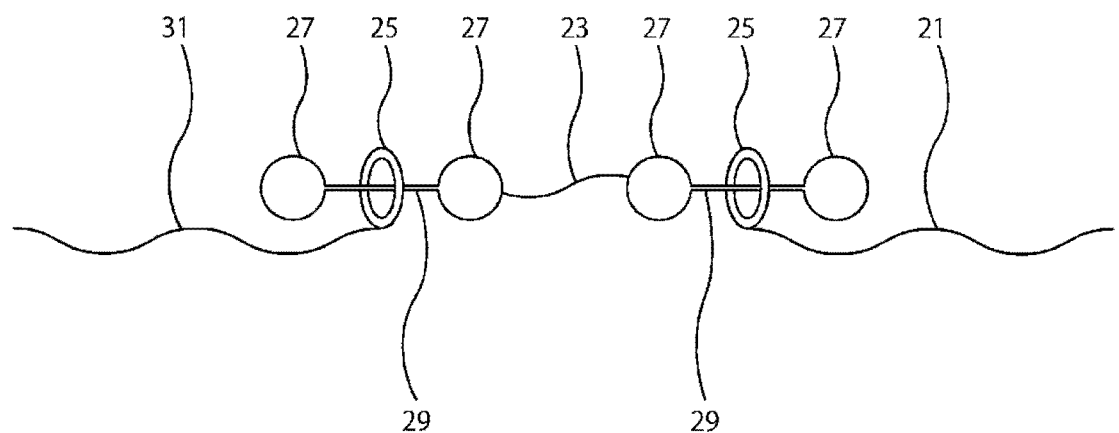
FIG. 6 is an illustrative figure schematically illustrating a structure of the polyurethane according to the present invention.

FIG. 6 is an illustrative figure schematically illustrating another embodiment of the polyurethane according to the present invention further comprising a third urethane short chain 31 in addition to the first and second urethane short chains. The second urethane short chain 23 has blocking structures 27 at one terminal thereof to block a cyclic structure 25 of a crown ether bonding to the first urethane short chain 21. The second urethane short chain 23 has blocking structures 27 at another terminal thereof to block a cyclic structure 25 of a crown ether bonding to the third urethane short chain 31.

The crown ether to which the urethane short chain bonds is a cyclic ether. Generally, the crown ether has a cyclic structure having an inner pore at the center, and the oxygen atom existing on the cyclic structure faces toward the inner pore. The oxygen atom of the cyclic structure of the crown ether electrostatically interacts with the cation, and thus the crown ether takes and keeps the cation in the inner pore. In other words, the crown ether is known as a so-called host-guest compound.

The atom constituting the cyclic structure of the crown ether preferably includes a carbon atom and an oxygen atom.

The number of the atoms constituting the cyclic structure of the crown ether is preferably 12 or more, more preferably 15 or more, and is preferably 34 or less, more preferably 32 or less. In addition, among the number of the atoms constituting the cyclic structure, the number of the oxygen atoms is preferably 4 or more, more preferably 6 or more, and is preferably 12 or less, more preferably 10 or less. One to three atoms of the oxygen atoms constituting the cyclic structure are optionally replaced with NH, NR, or S.

A benzene ring is preferably introduced in the cyclic structure of the crown ether. The urethane short chain preferably bonds to the benzene ring of the cyclic structure of the crown ether.

Specific examples of the crown ether include dibenzo-24-crown-8, 24-crown-8, benzo-24-crown-8, and dicyclohexyl-24-crown-8. Among them, dibenzo-24-crown-8 and benzo-24-crown-8, each of which has a benzene ring in the cyclic structure, are preferable.

In the urethane short chain, the blocking structure for preventing disassociation of the cyclic structure of the crown ether from the chain molecule is located on both terminal sides of the chain portion with a little steric hindrance of the chain molecule to sandwich the cyclic structure of the crown ether. The blocking structure is not particularly limited, as long as it has a more bulky structure than the inner pore of the crown ether, and examples of the blocking structure include alkylbenzene, dialkylbenzene, trityl, terphenyl, anthracene, bistrifluoromethylbenzene, fullerene and porphyrin.

The number average molecular weight of the polyurethane according to the present invention is preferably 10,000 or more, more preferably 20,000 or more, and even more preferably 40,000 or more. If the number average molecular weight is equal to or higher than the above lower limit, the properties acting as a macromolecule are exerted. In addition, the molecular weight dispersity (PDI) is preferably 4.0 or less, more preferably 3.0 or less.

EXAMPLES

Next, the present invention will be described in detail by way of examples. However, the present invention is not limited to the examples described below. Various changes and modifications without departing from the spirit of the present invention are included in the scope of the present invention.
[Test Method]
[$^1$HNMR]
NMR was measured with a Bruker AVANCEIIIHD500 spectrometer.
[MALDI-TOF-MS]
MALDI-TOF-MS was measured with AXIMA-CFR available from Shimadzu in a linear-positive ion mode, by using dithranol as a matrix and sodium trifluoroacetate as a cationization agent.
[Molecular Weight]
Molecular weight was obtained by size exclusion chromatograph. Number average molecular weight, weight average molecular weight and dispersity were values based on polystyrene conversion.
Measuring conditions are as follows.
Column: TOSOH TSKgel G2500H and G4000H
Pump: Intelligent HPLC pump PU-2080 available from JASCO Corporation
Eluate: N,N-dimethyl formamide (DMF) in which 5 mM of LiBr was added (30° C., flow: 0.7 mL)
Detector: RI (differential refractometer)

[Modulus of Elasticity]

Modulus of elasticity was calculated by proximately linearizing any linear region within 10% strain among the results of a tensile test (SHIMADZU EZ-S, sample shape: #JIS 7, tensile speed: 40 mm/min, 25° C.).

[Yield]

Yield was calculated from the weight charged in the reaction and the weight of the dried sample (vacuum dried at 80° C. for 12 hours).

Yield (%)=100×weight of dried sample/weight charged in reaction

The rotaxane was synthesized according to the method shown in the following scheme 1 and scheme 2.

Scheme 1
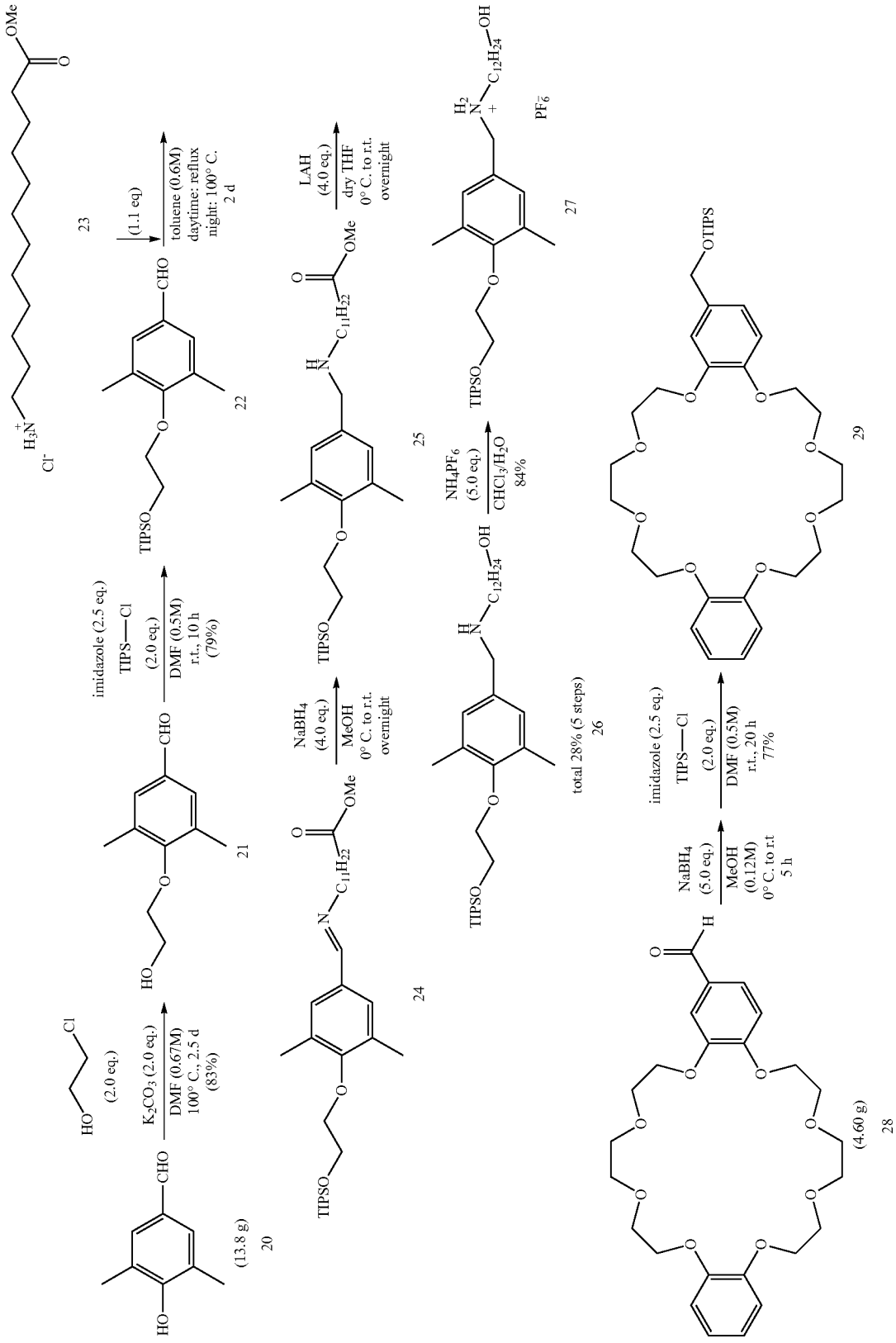

Scheme 2
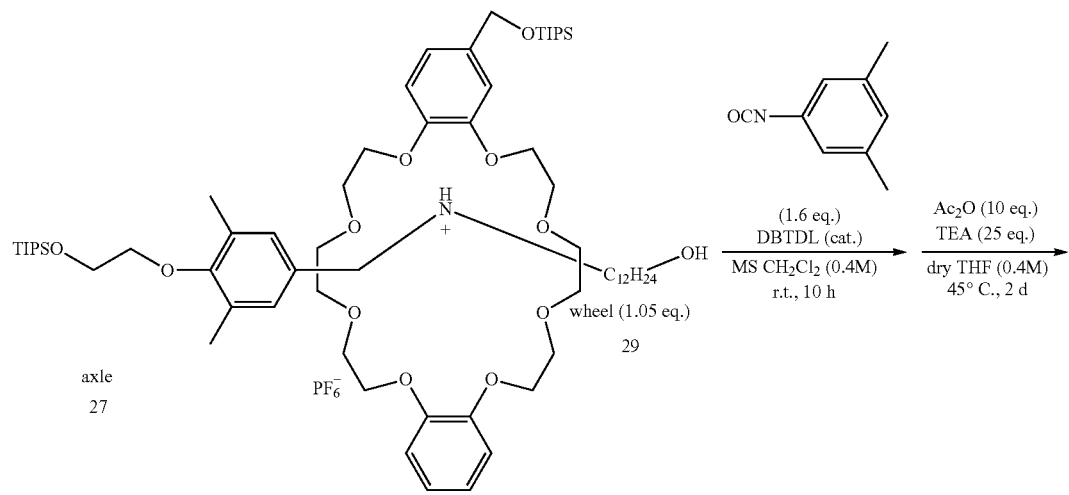
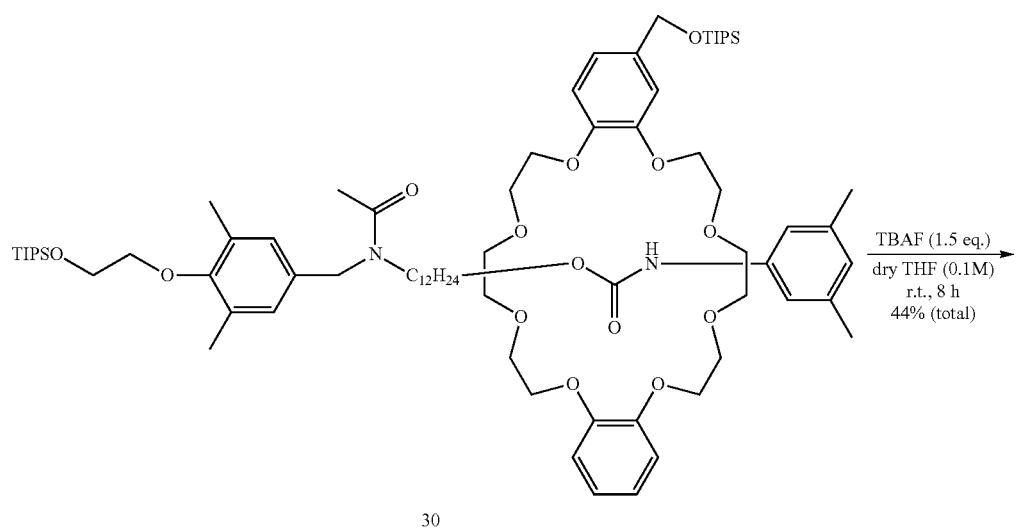
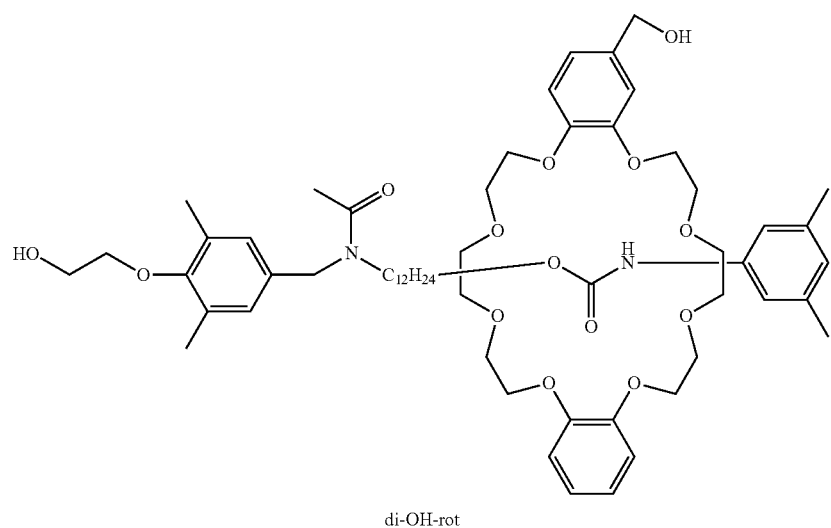

(1) Synthesis of Chain Molecule
Synthesis of 21

In 3,5-dimethyl-4-hydroxybenzaldehyde (13.8 g: 91.9 mmol), 2-chloroethanol (15.0 g, 187 mmol) and potassium carbonate (24.2 g, 175 mmol), N,N-dimethylformamide (DMF) (130 mL) was added, and stirred at 100° C. for 2.5 days. Disappearance of the raw materials ($R_f$: 0.6) was confirmed by TLC (ethyl acetate/hexane=1/2 (v/v)), and the solvent was removed by distillation. The residue was dissolved in dichloromethane, filtered to remove an inorganic salt, and then washed (1M HCl aq.→sodium bicarbonate water for 2 times→saturated sodium chloride solution), to obtain a crude product 21 (14.8 g).

Synthesis of 22

In the crude product 21 (total amount obtained above), imidazole (13.0 g, 190 mmol) and triisopropylsilyl chloride (TIPS-Cl) (32.6 mL, 29.4 g, 152 mmol), DMF (150 mL) was added, and stirred at room temperature for 10 hours. Disappearance of the raw materials ($R_f$: 0.2) was confirmed by TLC (ethyl acetate/hexane=1/1 (v/v)), and the solvent was removed by distillation. The residue was dissolved in dichloromethane, and washed (sodium bicarbonate water for 2 times→saturated sodium chloride solution), to obtain a crude product 22 (21.1 g).

Synthesis of 25

In the crude product 22 (total amount obtained above) and a hydrochloride 23 (17.6 g, 66.2 mmol), toluene (100 mL) was added, and stirred at reflux (100° C. at night) for 2 days. After the reaction, the solvent was removed by distillation. Methanol (300 mL) was added in the residue, and NaBH$_4$ (9.14 g, 242 mmol) was added therein under an ice bath condition and directly stirred overnight. Disappearance of the imine peak was confirmed by $^1$HNMR, and the solvent was removed by distillation. The residue was dissolved in dichloromethane, washed (saturated sodium chloride solution→methanol for 2 times), and purified with silica gel column chromatography (ethyl acetate/hexane=1/3→1/1→chloroform/methanol=20/1→10/1→9/1 (v/v)), to obtain 25 (32.7 g, 58.0 mmol).

$^1$HNMR (500 MHz, 298 K, CDCl$_3$): δ7.21 (s, 2H), 4.01 (t, J=4.6 Hz, 2H), 3.90 (s, 2H), 3.80 (t, J=4.6 Hz, 2H), 3.66 (s, 3H), 2.72 (t, J=8.4 Hz, 2H), 2.29 (s, 6H), 2.29 (t, 2H), 1.89-1.79 (m, 2H), 1.65-1.55 (m, 2H), 1.35-1.00 (m, 35H) ppm.

Synthesis of 26

In lithium aluminum hydride (LAH) (4.20 g, 111 mmol), dry tetrahydrofuran (THF) (500 mL) was added, and dry tetrahydrofuran (THF) solution (50 mL) of 25 (No. 953, total amount) was slowly added dropwise under an ice bath condition, and directly stirred overnight. After the reaction, sodium sulfate aqueous solution, methanol and pure water were used to inactivate (quench) the unreacted lithium aluminum hydride (LAH), filtrated to remove Al salt, and purified with silica gel column chromatography (dichloromethane/methanol=1/0→39/1→20/1 (v/v)), to obtain a white product 26 (13.6 g, 25.4 mmol, 25%).

$^1$HNMR (500 MHz, 298 K, CDCl$_3$): δ6.95 (s, 2H), 4.03 (t. J=5.2 Hz, 2H), 3.85 (t. J=5.2 Hz, 2H), 3.66 (s, 2H), 3.64 (t, J=6.6 Hz, 2H), 2.62 (t. J=7.3 Hz, 2H), 2.28 (s, 6H), 1.60-1.47 (m, 4H), 1.38-1.23 (m, 16H), 1.19-1.06 (m, 21H) ppm.

Synthesis of 27

In 26 (2.19 g, 4.09 mmol), chloroform (CHCl$_3$) (30 mL) was added to dissolve 26, and the resulting solution was moved to a separatory funnel. NH$_4$PF$_6$ (3.33 g, 20.4 mmol) aqueous solution (30 mL) was added, and mixed by strong shaking. After the operation was repeated, drying was performed with sodium sulfate, to obtain a yellow solid 27 (2.34 g, 3.43 mmol, 84%).

$^1$HNMR (500 MHz, 298 K, CDCl$_3$): δ7.02 (s, 2H), 4.03 (t, J=5.2 Hz, 2H), 3.97 (br, 2H), 3.86 (t, J=5.2 Hz, 2H), 3.61 (t, J=6.6 Hz, 2H), 2.82 (t, J=7.9 Hz, 2H), 2.30 (s, 6H), 1.67-1.58 (m, 4H), 1.37-1.19 (m, 16H), 1.19-1.05 (m, 21H) ppm.

(2) Preparation of Crown Ether
Synthesis of 29

In monoformyl crown ether 28 (4.60 g, 9.65 mmol), methanol (80 mL) was added, and NaBH$_4$ (1.80 g, 47.6 mmol) was added and directly stirred for 5 hours under an ice bath condition. Disappearance of the aldehyde peak was confirmed by $^1$HNMR, and the solvent was removed by distillation. Water was added in the residue, the residue was extracted (dichloromethane for 2 times) and washed (sodium bicarbonate water→saturated sodium chloride solution), and the solvent was removed again by distillation to dry the residue. Subsequently, in imidazole (1.64 g, 24.1 mmol) and triisopropylsilyl chloride (TIPS-Cl) (4.1 mL, 3.72 g, 19.3 mmol), N,N-dimethylformamide (DMF) (20 mL) was added and stirred at room temperature for 20 hours, followed by further performing the reaction at 35° C. for 5 hours. After the solvent was removed by distillation, the residue was dissolved in dichloromethane, washed (ammonium chloride aqueous solution→sodium bicarbonate water→saturated sodium chloride solution), and purified with silica gel column chromatography (ethyl acetate/hexane=1/1), to obtain a white solid 29 (4.74 g, 7.46 mmol, 77%).

$^1$HNMR (500 MHz, 298 K, CDCl$_3$): δ6.92 (s, 1H), 6.90-6.85 (m, 4H), 6.83-6.82 (br, 2H), 4.74 (s, 2H), 4.18-4.12 (m, 8H), 3.94-3.89 (m, 8H), 3.86-3.82 (m, 8H), 1.21-1.12 (m, 3H), 1.11-1.06 (m, 18H) ppm.

(3) Preparation of Rotaxane
Synthesis of Rotaxane 30 Having a Triisopropylsilyl (TIPS) Group on Each of the Cyclic Structure and the Chain Molecule In the axis component 27 (2.55 g, 3.74 mmol) and the wheel component 29 (2.49 g, 3.92 mmol), dehydrated dichloromethane (10 mL) was added, and ultrasonic radiation was conducted to form a complex. Subsequently, 3,5-dimethylphenylisocyanate (0.92 g, 6.3 mmol) and dibutyl tin dilaurate (DBTDL) (some drops) were added, and stirred at room temperature for 10 hours to perform terminal blocking. Completion of the terminal blocking was confirmed by MALDI-TOF-MS, and methanol was added to inactivate (quench) the excessive isocyanate. After the reaction solution was fully dried with an evaporator and subsequently a vacuum line, triethylamine (TEA) (9.90 g, 97.8 mmol), acetic acid anhydride (4.00 g, 39.2 eq.) and dehydrated tetrahydrofuran (THF) (10 mL) were added to dissolve the residue, and stirred at 45° C. for 2 days. After termination of the reaction was confirmed by MALDI-TOF-MS and the solvent was removed by distillation, ethyl acetate was added, and the residue was washed (ammonium chloride aqueous solution for 1 time→sodium bicarbonate water for 1 time→saturated sodium chloride solution for 1 time), and purified with silica gel column chromatography (dichloromethane/ethyl acetate=10/1), to obtain a rotaxane 30 having triisopropylsilyl (TIPS) group on each of the cyclic structure and the chain molecule (4.17 g, 3.06 mmol).

Synthesis of Rotaxane Having a Hydroxyl Group on Each of the Cyclic Structure and the Chain Molecule (Hereinafter Referred to as "Rotaxane Diol" Occasionally)

In the rotaxane 30 (total amount), tetra n-butylammonium fluoride (TBAF) (1M tetrahydrofuran (THF) solution) (9.2 mL) and dehydrated tetrahydrofuran (THF) (20 mL) were added, and stirred at room temperature for 8 hours. After termination of the reaction was confirmed by MALDI-TOF-MS and the solvent was removed by distillation, ethyl acetate was added, and the residue was washed (NH$_4$Cl aq.x2, brine), and purified with silica gel column chromatography (Eluent: ethyl acetate/dichloromethane=1/3→ethyl acetate/methanol=30/1 (v/v)) and separatory GPC (Eluent: chloroform), to obtain a rotaxane diol (1.79 g, 1.71 mmol, 44%).

$^1$HNMR (500 MHz, 298K, CDCl$_3$): δ8.34 (d, J=28.1 Hz, 1H), 7.16 (s, 2H), 6.91-6.78 (m, 9H), 6.51 (s, 1H), 4.62-4.58 (m, 2H), 4.44 (d, J=29.6 Hz, 2H), 4.36-4.30 (m, 2H), 4.22-4.05 (m, 8H), 3.97-3.78 (m, 12H), 3.59-3.56 (m, 8H), 3.25 (dt, J=80.9, 7.9 Hz, 2H), 2.27 (d, J=11.7 Hz, 6H), 2.14 (d, J=27.9 Hz, 3H), 2.09 (s, 6H), 1.58-1.47 (m, 2H), 1.47-1.38 (m, 2H), 1.28-0.92 (m, 16H) ppm.

Figure 7:
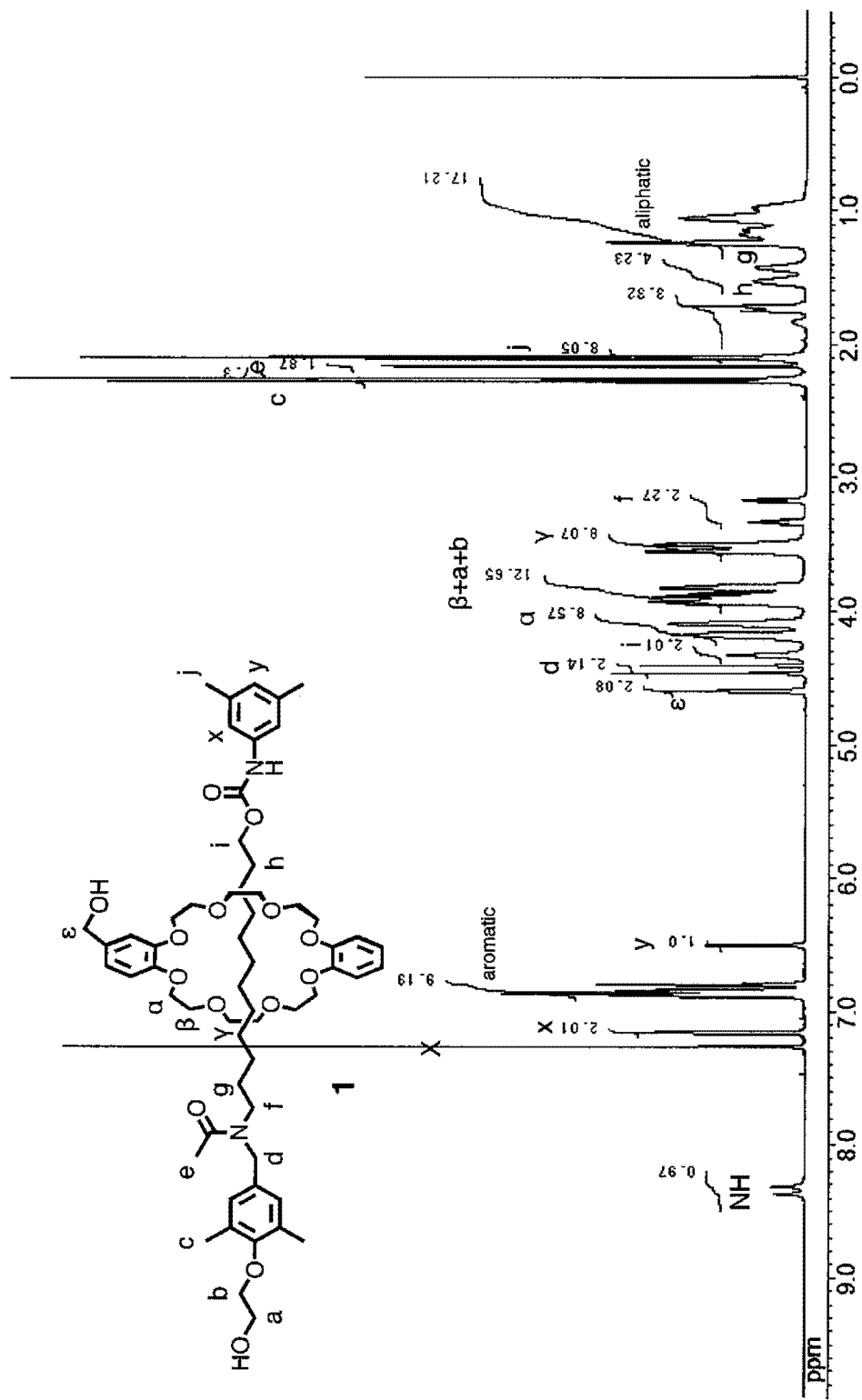
FIG. 7 is a $^1$HNMR spectrum of one example of the rotaxane according to the present invention.
Figure 8:
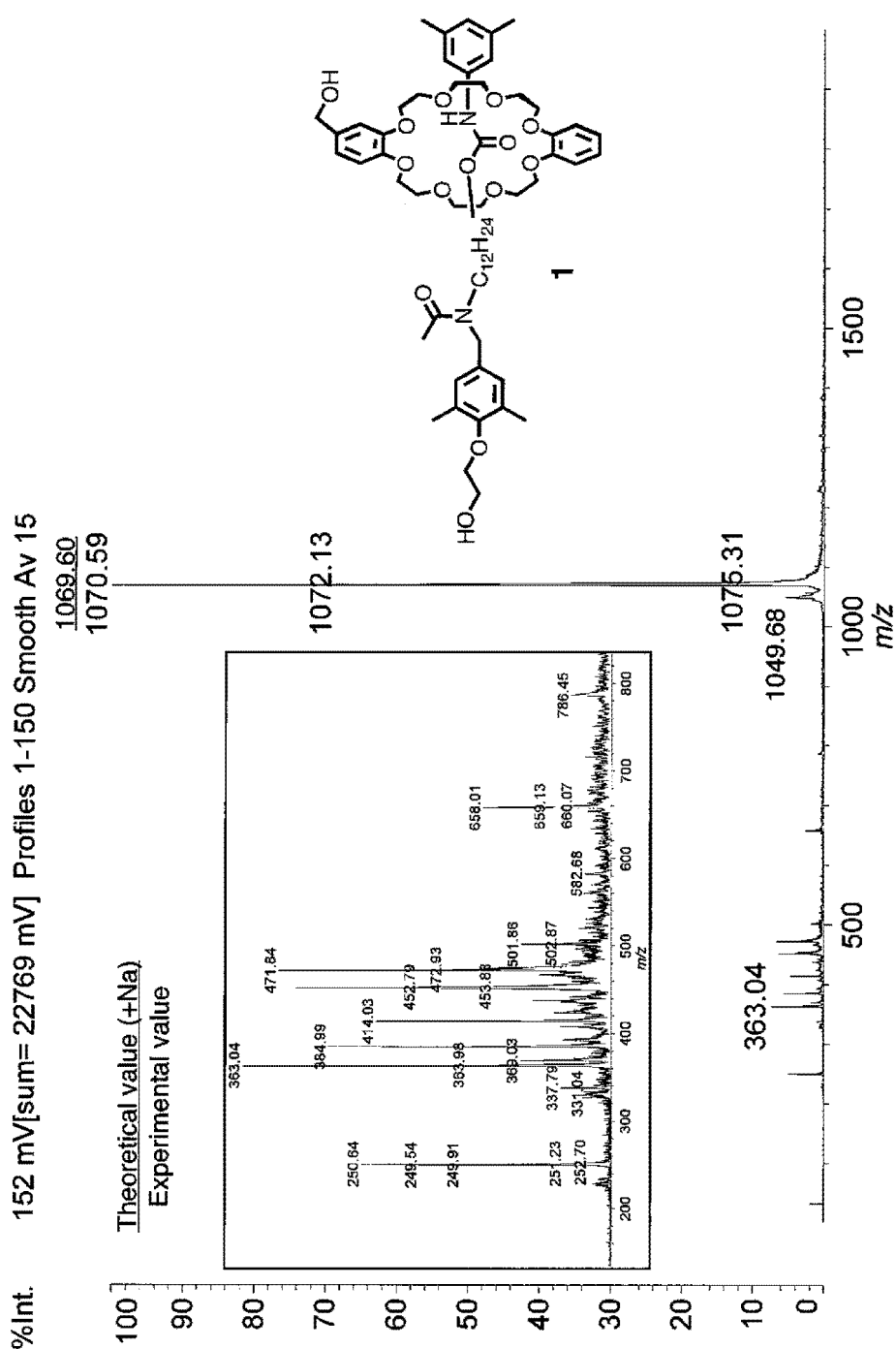
FIG. 8 is a MALDI-TOF-MS spectrum of one example of the rotaxane according to the present invention.

$^1$HNMR (500 MHz, 298 K, CDCl$_3$) measurement result of the obtained rotaxane diol is shown in FIG. 7. In addition, MALDI-TOF-MS measurement spectrum is shown in FIG. 8.

The obtained rotaxane diol was used to synthesize a polyurethane.

Synthesis Conditions and Properties of the Obtained Polyurethane are Shown in Tables 1-4 in Combination

TABLE 1

| Pu No. | Synthesis of prepolymer | | | | | Chain extension reaction | | | | Molecular weight | | |
|---|---|---|---|---|---|---|---|---|---|---|---|---|
| | PTHF 1000 | Rotaxane diol | HDI | Temp. (° C.) | Time (h) | Butanediol | Temp. (° C.) | Time (h) | Yield (%) | Mn (KDa) | Mw (KDa) | PDI |
| 1 | 1 | — | 2 | 25 | 3 | 1 | 25 | 24 | 37 | 35 | 50 | 1.43 |
| 2 | 1 | — | 2 | Rt. | 3 | 1 | Rt. | 24 | 38 | 39 | 58 | 1.49 |
| 3 | 1 | — | 2 | 25 | 8.5 | 1 or more | 25 | 17 | — | 20 | 29 | 1.44 |
| 4 | 1 | — | 2 | Rt. | 10 | 1 | Rt. | 27 | 73 | 62 | 93 | 1.50 |
| 5 | 0.9 | 0.1 | 2 | 25 | 7 | 1 | 25 | 15.5 | 64 | 11 | 22 | 2.06 |
| 6 | 1.5 | — | 2 | 25 | 7 | 0.5 | 25 | 15.5 | 80 | 20 | 36 | 1.84 |
| 7 | 1.2 | — | 2 | 25 | 12 | 0.8 | 25 | 12 or more | 51 | 28 | 43 | 1.54 |
| 8 | 0.9 | 0.1 | 2 | 60 | 8 | 1 | 60 | 16 | 72 | 8.3 | 14 | 1.65 |
| 9 | 0.8 | 0.1 | 2 | 60 | 8 | 1 | 60 | 16 | 73 | 8.4 | 15 | 1.78 |

Raw material ratio: molar ratio

Rt: Room temperature

TABLE 2

| Pu No. | Synthesis of prepolymer | | | | | Chain extension reaction | | | | | Molecular weight | | |
|---|---|---|---|---|---|---|---|---|---|---|---|---|---|
| | PTHF 2900 | Rotaxane diol | HDI | Temp. (° C.) | Time (h) | Rotaxane diol | Butanediol | Temp. (° C.) | Time (h) | Yield (%) | Mn (KDa) | Mw (KDa) | PDI |
| 10 | 1 | — | 2 | 25 | 12 | — | 1 | 25 | 12 or more | 79 | 84 | 130 | 1.55 |
| 11 | 1 | — | 2 | 60 | 6 | 0.1 | 0.9 | 60 | 12 or more | 68 | 53 | 73 | 1.37 |
| 12 | 0.9 | 0.1 | 2 | 60 | 6 | — | 1 | 60 | 12 or more | 63 | 52 | 71 | 1.37 |

Raw material ratio: molar ratio

TABLE 3

| | Synthesis of prepolymer | | | | | | | | Molecular weight | | |
|---|---|---|---|---|---|---|---|---|---|---|---|
| Pu No. | PTHF2000 | Rotaxane diol | HDI | Temp. (° C.) | Time (h) | Butanediol | Temp. (° C.) | Time (h) | Yield (%) | Mn (KDa) | Mw (KDa) | PDI |
| 13 | 1 | — | 2 | 60 | 14 | 1 | 60 | 12 | 60 | 54 | 97 | 1.78 |
| 14 | 0.9 | 0.1 | 2 | 60 | 14 | 1 | 60 | 12 | 14 | 31 | 47 | 1.53 |
| 15 | 1 | — | 2 | 60 | 6 | 1 | 60 | 16 | 80 | 35 | 65 | 1.85 |
| 16 | 1 | — | 2 | 60 | 6 | 1 | 60 | 13 | 83 | 43 | 82 | 1.93 |

Raw material ratio: molar ratio

TABLE 4

| | Synthesis of prepolymer | | | | | Chain extension reaction | | | | | Molecular weight | | |
|---|---|---|---|---|---|---|---|---|---|---|---|---|---|
| Pu No. | PTHF 1400 | Rotaxane diol | HDI | Temp. (° C.) | Time (h) | Rotaxane diol | Butanediol | Temp. (° C.) | Time (h) | Yield (%) | Mn (KDa) | Mw (KDa) | PDI |
| 17 | 0.95 | 0.05 | 2 | 60 | 4.5 | — | 1 | 60 | 6 | 83 | 17.3 | 31.0 | 1.79 |
| 18 | 0.975 | 0.025 | 2 | 60 | 4.5 | — | 1 | 60 | 6 | 96 | 18.1 | 33.8 | 1.87 |
| 19 | 0.985 | 0.015 | 2 | 60 | 4.5 | — | 1 | 60 | 6 | 94 | 16.0 | 27.6 | 1.72 |
| 20 | 0.99 | 0.01 | 2 | 60 | 4.5 | — | 1 | 60 | 6 | 89 | 18.1 | 46.3 | 2.56 |
| 21 | 1 | — | 2 | 60 | 4.5 | — | 1 | 60 | 6 | 91 | 12.1 | 24.3 | 2.01 |
| 22 | 1 | — | 2 | 60 | 4.5 | 0.015 | 0.985 | 60 | 6 | 94 | 17.1 | 30.4 | 1.77 |
| 23 | 1 | — | 2 | 60 | 4.5 | 0.025 | 0.975 | 60 | 6 | 91 | 10.4 | 21.6 | 2.07 |
| 24 | 1 | — | 2 | 60 | 4.5 | 0.05 | 0.95 | 60 | 6 | 95 | 17.8 | 33.4 | 1.87 |

Raw material ratio: molar ratio

HDI: hexamethylene diisocyanate available from Wako Pure Chemical Corporation

PTHF1000: polytetrahydrofuran (number average molecular weight: 1000) available from Sigma-aldrich Corporation PTHF1400: polytetrahydrofuran (number average molecular weight: 1400) available from Sigma-aldrich Corporation PTHF2000: polytetrahydrofuran (number average molecular weight: 2000) available from Sigma-aldrich Corporation PTHF2900: polytetrahydrofuran (number average molecular weight: 2900) available from Sigma-aldrich Corporation Butanediol: available from Wako Pure Chemical Corporation Films were prepared from the obtained polyurethanes 10, 11, 12, 13, 15-24, and mechanical properties thereof were measured. Results are shown in Table 5. S-S curves of the polyurethanes 10, 11, 12 are shown in FIGS. 9-10.

TABLE 5

| | Mechanical properties | | | | |
|---|---|---|---|---|---|
| Pu No. | Thickness of film (μm) | Young's modulus of elasticity (MPa) | Breaking elongation (%) | Breaking stress (MPa) | Breaking energy (MJ/m³) |
| 10 | 240 | 10 | 1020 | 38 | 130 |
| 11 | 460 | 3.2 | 1060 | 32 | 130 |
| 12 | 390 | 2.7 | 1090 | 24 | 120 |
| 13 | 230 | 21 | 1090 | 50 | 220 |
| 15 | 260 | 4.3 | 1160 | 26 | 160 |
| 16 | 150 | 4.6 | 1020 | 32 | 150 |
| 17 | 270 | 10 | 50 | 2.6 | 0.9 |
| 18 | 270 | 13 | 120 | 4.0 | 3.7 |
| 19 | 290 | 12 | 100 | 3.2 | 2.5 |
| 20 | 330 | 11 | 90 | 3.6 | 2.2 |
| 21 | 260 | 22 | 60 | 3.2 | 1.4 |
| 22 | 300 | 11 | 50 | 2.6 | 1.0 |
| 23 | 330 | 8.2 | 150 | 3.3 | 3.8 |
| 24 | 310 | 14 | 40 | 2.6 | 0.8 |

Figure 9:
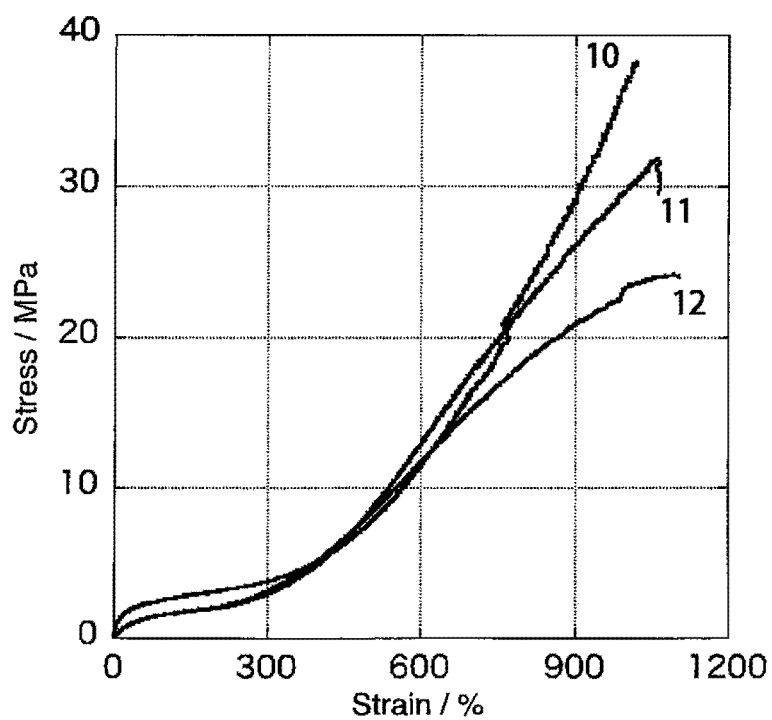
FIG. 9 is an SS curve of the polyurethane No. 10, 11 and 12.
Figure 10:
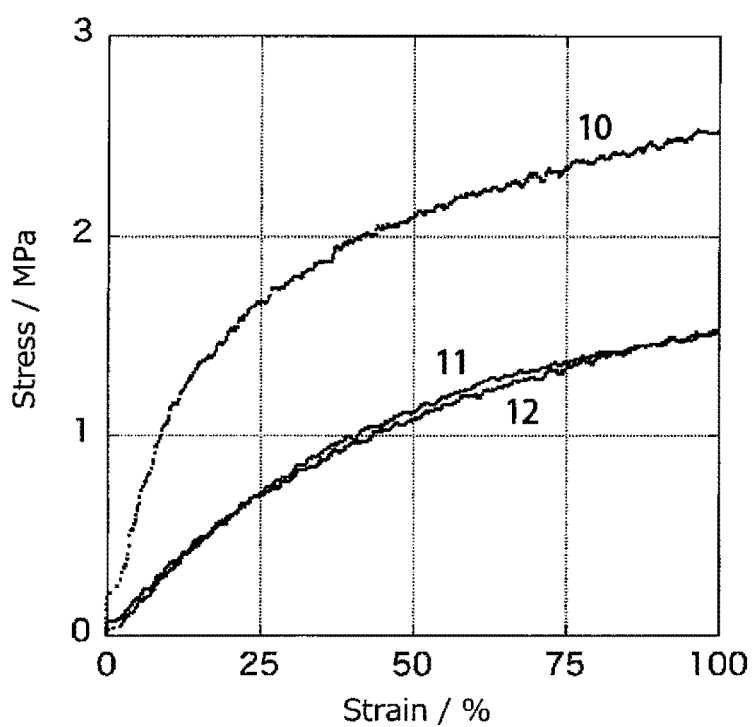
FIG. 10 is an amplification figure of FIG. 9.

It is known from Table 5 and FIGS. 9-10 that the polyurethane according to the present invention having a rotaxane introduced is soft and tough.

This application is based on Japanese Patent application No. 2018-103437 filed on May 30, 2018, the content of which is hereby incorporated by reference.

The invention claimed is:

1. A rotaxane having a crown ether and a chain molecule piercing through the cyclic structure of the crown ether, wherein the rotaxane has a structure with a hydroxyl group existing at one terminal of the chain molecule and a hydroxyl group bonding to the cyclic structure of the crown ether.

2. The rotaxane according to claim 1, wherein the crown ether has a cyclic structure having a benzene ring, and the hydroxyl group bonds to the benzene ring of the cyclic structure.

3. The rotaxane according to claim 1, wherein the rotaxane is a diol having two hydroxyl groups.

4. The rotaxane according to claim 1, having a structure represented by the following structural formula (1):

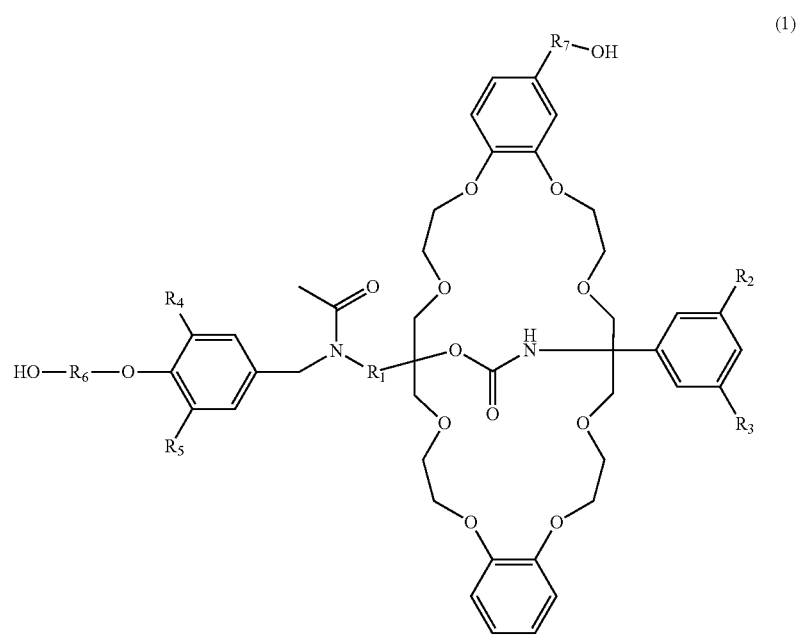

(1)

in the formula (1), $R_1$ represents an alkylene chain having 3 to 30 carbon atoms;

$R_2$, $R_3$, $R_4$, $R_5$ may be identical to or different from each other and represent an alkyl group having 1 to 10 carbon atoms;

$R_6$ represents an alkylene chain having 1 to 10 carbon atoms; and $R_7$ represents a single bond or an alkylene chain having 1 to 6 carbon atoms.

5. A polyurethane comprising a polyisocyanate component and a rotaxane component as a constituent component, wherein the rotaxane component is a rotaxane having a crown ether and a chain molecule piercing through the cyclic structure of the crown ether, wherein the rotaxane component has a structure with a hydroxyl group existing at one terminal of the chain molecule and a hydroxyl group bonding to the cyclic structure of the crown ether.

6. The polyurethane according to claim 5, wherein the crown ether has a cyclic structure having a benzene ring, and the hydroxyl group bonds to the benzene ring of the cyclic structure.

7. The polyurethane according to claim 5, wherein the rotaxane is a diol having two hydroxyl groups.

8. The polyurethane according to claim 5, wherein the polyurethane further comprises a polyol component in addition to the rotaxane component.

9. The polyurethane according to claim 8, wherein the polyol component includes a high molecular weight polyol and/or a low molecular weight polyol.

10. A polyurethane at least comprising a first urethane short chain and a second urethane short chain, wherein the first urethane short chain bonds to a cyclic structure of a crown ether at one terminal of the first urethane short chain, the second urethane short chain pierces through the cyclic structure of the crown ether of the first urethane short chain, and has blocking structures on both sides of the cyclic structure of the crown ether to prevent disassociation of the cyclic structure of the crown ether of the first urethane short chain from the second urethane short chain.

11. The polyurethane according to claim 5, wherein the rotaxane has a structure represented by the following structural formula (1):

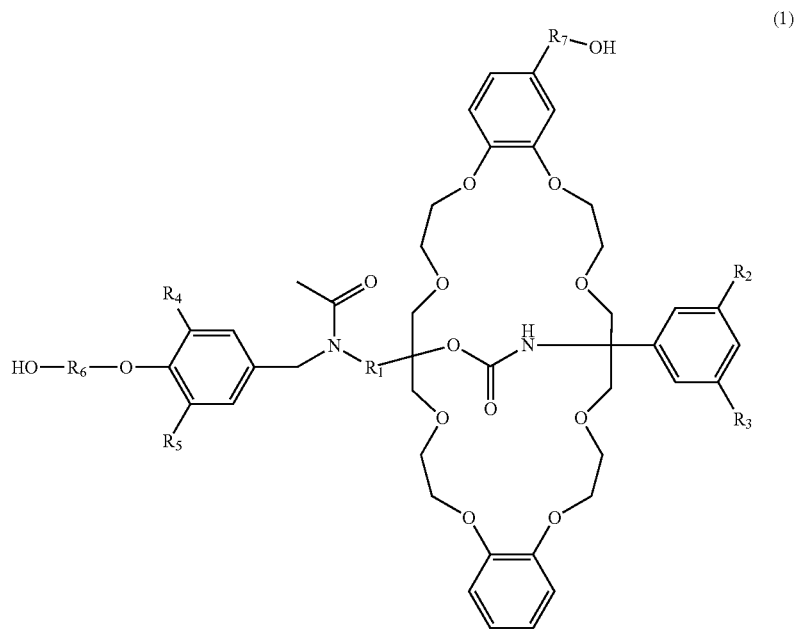
in the formula (1), $R_1$ represents an alkylene chain having 3 to 30 carbon atoms;
$R_2$, $R_3$, $R_4$, $R_5$ may be identical to or different from each other and represent an alkyl group having 1 to 10 carbon atoms;
$R_6$ represents an alkylene chain having 1 to 10 carbon atoms; and
$R_7$ represents a single bond or an alkylene chain having 1 to 6 carbon atoms.
* * * * *